(12) United States Patent
Duriez et al.

(10) Patent No.: US 6,443,001 B1
(45) Date of Patent: Sep. 3, 2002

(54) METHOD AND SYSTEM FOR EXTRACTING, ANALYZING AND MEASURING CONSTITUENTS TRANSPORTED BY A BORE FLUID

(75) Inventors: Gilbert Duriez, Rueil-Malmaison; Jean-Paul LeCann, Dammartin en Goële; Jérôme Breviere, Saint Brice sous Foret; Jean-Charles de Hemptinne, Le Vesinet, all of (FR)

(73) Assignee: Institut Francais du Petrole, Rueil-Malmaison Cedex (FR)

( * ) Notice: Subject to any disclaimer, the term of this patent is extended or adjusted under 35 U.S.C. 154(b) by 0 days.

(21) Appl. No.: 09/831,275
(22) PCT Filed: Sep. 14, 2000
(86) PCT No.: PCT/FR00/02543
§ 371 (c)(1), (2), (4) Date: May 9, 2001
(87) PCT Pub. No.: WO01/22050
PCT Pub. Date: Mar. 29, 2001

(30) Foreign Application Priority Data

Sep. 24, 1999 (FR) .............................. 99/12032

(51) Int. Cl.$^7$ .............. E21B 21/08; G01N 33/497; G01N 1/00; G01N 33/00
(52) U.S. Cl. ............. 73/152.19; 73/19.01; 73/863.12; 436/30
(58) Field of Search ................. 73/152.19, 152.23, 73/19.01, 19.09, 23.38, 863.12; 96/174; 205/787; 436/30

(56) References Cited

U.S. PATENT DOCUMENTS

| | | | | | |
|---|---|---|---|---|---|
| 2,362,805 A | * | 11/1944 | Doan | .......................... | 436/30 |
| 2,370,817 A | * | 3/1945 | Shanley | ...................... | 73/19.09 |
| 2,398,580 A | * | 4/1946 | Crawford | ..................... | 436/30 |
| 2,591,737 A | * | 4/1952 | Souther | ....................... | 250/255 |
| 2,715,450 A | * | 8/1955 | Bliss et al. | ................... | 96/174 |
| 3,196,664 A | * | 7/1965 | Teal | .......................... | 73/23.38 |
| 3,240,068 A | * | 3/1966 | Horeth et al. | ............ | 73/863.12 |
| 3,342,558 A | * | 9/1967 | Reinecke | ..................... | 205/787 |
| 3,381,536 A | * | 5/1968 | Horeth et al. | ............ | 73/863.12 |
| 3,418,841 A | * | 12/1968 | Isenmann | .................... | 73/19.01 |

FOREIGN PATENT DOCUMENTS

WO        0049269     *  8/2000  ........... E21B/21/06

* cited by examiner

*Primary Examiner*—Hezron Williams
*Assistant Examiner*—Jay L. Politzer
(74) *Attorney, Agent, or Firm*—Antonelli, Terry, Stout & Kraus, LLP

(57) ABSTRACT

The present invention relates to an extraction, analysis and measuring method and system intended for constituents carried along by a well fluid during drilling operations. The system comprises in combination: draw-off means (4) for taking a volume of the fluid, extraction means (3) for extracting in vapour form the constituents contained in the fluid, comprising a space placed under underpressure, a transport line (14), sampling means (27) comprising a sampling loop allowing to take a determined amount of the vapors circulating in the line, distribution means (40) that inject the amount into analysis and measuring means (31), control means (33) for controlling the temperature of the sampling means so as to prevent condensation of said amount of vapors.

11 Claims, 2 Drawing Sheets

METHOD AND SYSTEM FOR EXTRACTING, ANALYZING AND MEASURING CONSTITUENTS TRANSPORTED BY A BORE FLUID

FIELD OF THE INVENTION

The present invention relates to a method and to a system intended for analysis and measurement of liquid or gaseous constituents contained in a drilling fluid. The term constituents designates here hydrocarbons, for example C1 to C8, including benzene, toluene, xylene, or gases such as $H_2S$, $CO_2$, $O_2$, $H_2$, $N_2$. These constituents are due to drilling operations carried out through formation layers, operations that have the effect of breaking the rock, thereby releasing the gases or the fluids contained in the rock pores. Drilling is conventionally carried out with a circulation of a fluid referred to as drilling fluid whose function, among others, is to clean the drill bit and to drive the rock debris up to the ground surface. The constituents in question are therefore also carried along to the surface by means of this carrier. It is clear that, considering the flow rate of the drilling fluid compared to the rate of destruction of the rock, the volume amount of said constituents is always relatively low compared to the volume of mud.

BACKGROUND OF THE INVENTION

There are known installations allowing to carry out qualitative and quantitative measurements of the C1–C5 gas contained in a drilling fluid, measurements (or logging operations) allowing to identify the geologic zones drilled for borehole and/or staff safety reasons. Document FR-2,646,508 describes a process and a device for continuous sampling of gaseous samples contained in a solid-containing liquid, notably a drilling fluid. In this document, neither its degassing mode nor its transportation mode allows to extract and to transport the hydrocarbons possibly present in liquid form in the mud carried along to the ground surface.

SUMMARY OF THE INVENTION

The object of the present invention is to implement the conditions required for: extraction of gaseous or liquid constituents contained in a drilling fluid, transportation of these constituents in gaseous form, and analyses and measurements of these constituents. In order to carry out correct analyses, allowing to better determine the nature and the composition of the formations crossed by a borehole, the constituents must not condense in the elements of the system and the time of transit of these constituents between the point of extraction and the point of measurement must be acceptable to allow the drilling operation to be monitored.

The present invention thus relates to an extraction, analysis and measuring system intended for constituents carried along by a well fluid during drilling operations. The system comprises in combination:

draw-off means for taking a determined volume of the fluid, extraction means for extracting, in vapour form, the constituents contained in the volume of fluid, comprising a space placed under underpressure, a vapour transport line, a first end of which communicates with the space, the second end being connected to a vacuum pump, sampling means placed in the vicinity of the second end, comprising a sampling loop that allows to sample a determined amount of the vapours circulating in said line, distribution means that inject the amount into analysis and measuring means, and means for controlling the temperature of the sampling means so as to prevent condensation of the amount of vapours.

The space that contains the drilling fluid drawn off can be sealed against the outer environment.

The space can comprise an inlet port for an auxiliary gas, air or nitrogen for example.

The extraction means can comprise means for heating said volume of fluid sampled.

The sampling loop can be mounted directly in parallel on the transport line.

The drilling fluid draw-off means can comprise a suction pump and/or a discharge pump.

The space can be at an absolute pressure ranging between 10 and 100 mb, and the suction of the vacuum pump can range between 1 and 10 mb.

The invention also relates to an extraction, analysis and measuring method intended for constituents carried along by a well fluid during drilling operations, wherein the following stages are carried out:

a volume of drilling fluid is drawn off and placed in a space belonging to extraction means intended for extraction of constituents in vapour form, an underpressure is applied in the space by means of a line connecting the analysis and measuring means to the extraction means, a determined amount of the vapours circulating in the line is drawn off in the vicinity of the analysis and measuring means, the amount of vapours is injected into the analysis and measuring means, the nature and/or the amount of the constituents vaporized in the extraction means is deduced.

According to the method, the underpressure and/or temperature conditions can be adjusted for extraction in vapour form as a function of the drilling parameters, for example the nature of the fluid, the flow rate, the ambient temperature, the time of transit in the line.

A feed flow rate of the auxiliary gas fed into the space can be adjusted.

An underpressure ranging between 10 and 100 mb in absolute pressure can be applied in the extraction space.

BRIEF DESCRIPTION OF THE DRAWINGS

Other features and advantages of the present invention will be clear from reading the description hereafter of a non limitative embodiment example, with reference to the accompanying drawings wherein.

DETAILED DESCRIPTION

Figure 1:
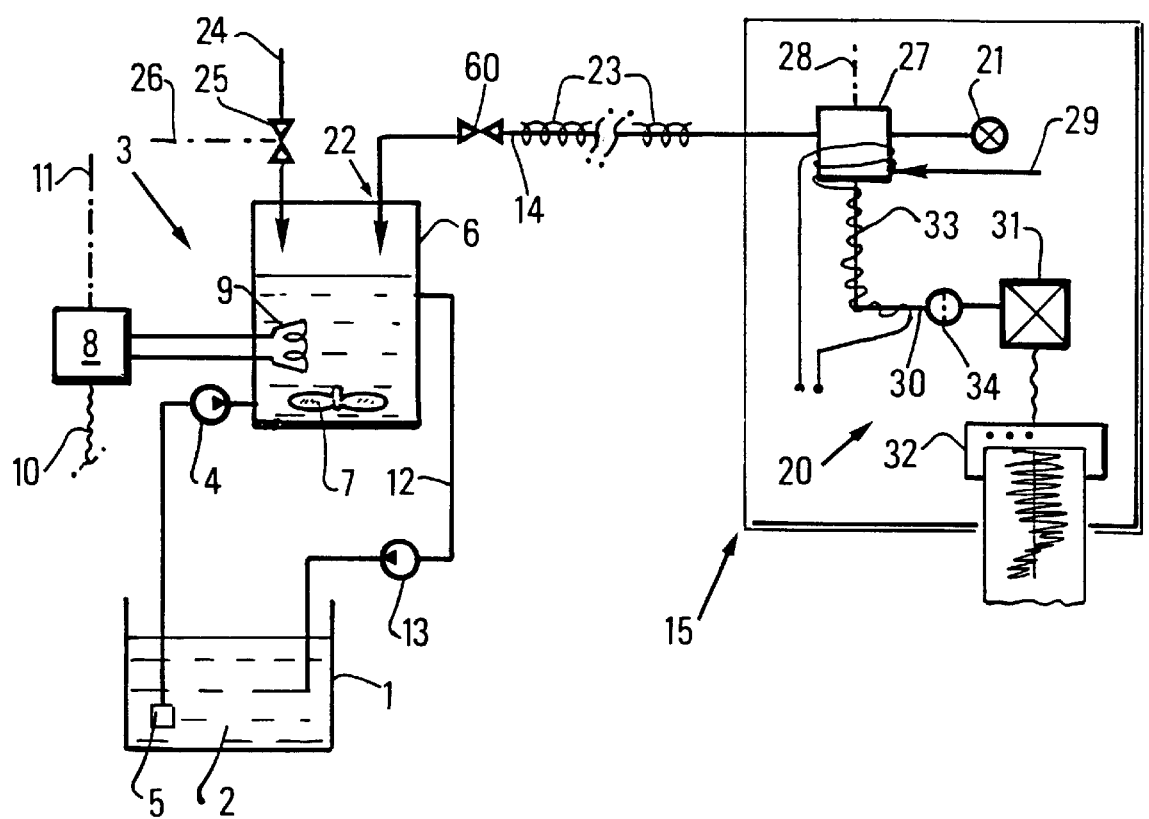
FIG. 1 is an overall view of the system according to the invention.

In FIG. 1, reference number 1 designates a flowline through which flows drilling fluid 2 returning from the well bottom by circulating in the annulus defined by the drill string and the wellbore. This flowline 1 leads the drilling fluid from the wellhead to the surface installation for treatment and separation of the solids. Extraction means 3 intended for the constituents to be analyzed preferably comprise a pump 4 whose inlet 5 plunges into the drilling fluid and whose discharge end opens into a vessel 6 whose volume allows to hold as a buffer a determined volume of fluid for a given time, said time depending on this volume and on the flow rate of pump 4. The volume of drilling fluid contained in vessel 6 is subjected to stirring in order to favour extraction through degassing and evaporation. This stirring operation can be mechanical, for example, by means of a rotating agitator 7, or ultrasonic means.

In order to obtain the desired extraction conditions, heating means 8 can comprise a heating rod 9 inside vessel 6, an electric power supply 10 and a control and regulation line 11. Other means for heating the volume of fluid in the vessel can be used, for example from outside, or a double heating wall. The vessel also comprises a mud discharge line 12 intended for the fluid flow taken by the pump and returning to the flowline. It is possible to place a pump 13 on this discharge line so as to better control the rate of circulation of the drilling fluid retained in vessel 6.

A line 14 connects extraction means 3 to analysis and measuring means 20. The length of this line can range between 50 and 200 m since measuring means 20 are placed in a cab (symbolized by frame 15) located at a sufficient distance from the wellhead to be in a secure zone. At the end of this line, a vacuum pump 21 creates an underpressure that can reach several millibars (1 to 10 mb for example). Considering the pressure drops and the circulating gas flow, the underpressure at the inlet 22 of the line can range for example between 10 and 100 mb. Underpressure control means 60 can be placed in the vicinity of the end of line 14, near extraction means 3. These means can be a valve, a choke, or any other means allowing to vary the underpressure in the line and/or vessel 6. The inside diameter of transport line 14 ranges between 5 and 15 mm, preferably about 10 mm. The material of the inner tube is selected to be impervious to hydrocarbons, such as for example fuel supply pipes. In order to prevent condensation of the gas conveyed, in certain extreme situations, it can be absolutely necessary to heat at least a portion of the wall, for example by means of a heating cord 23.

Vessel 6 comprises a gas inlet 24 for an inert gas or air, controlled by a valve 25 allowing to adjust the gas inflow rate. This valve can be controlled by means of a line 26.

In series on line 14, sampling means 27 for the conveyed gas flow sample a certain amount of gas according to a rate depending notably on the measuring cycle. The sampler is controlled by line 28. Sampling means 27 comprise: a loop referred to as <<chromatograph>> loop in which a volume of gas is taken from line 14, valves or distributors for carrying out this sampling operation, then for driving this volume of gas by pushing it with an inert fluid. These various constituents are detailed more precisely by means of FIGS. 3a and 3b. FIG. 1 diagrammatically shows injection line 29 for a carrier gas intended to displace the gas sample taken from line 14 by sampling means 27, delivery line 30 intended to lead this volume of gas into analyzer 31, for example a chromatography device. The measurements performed by means of device 31 are sent, by means of an electronic interface, to a central unit of a computer that processes these measurements in order to provide for example a record giving the nature and the amounts of the constituents carried along by the drilling fluid, according to the borehole depth.

At least a zone of sampling means 27 and a portion of line 30 can be heated by heating means 33 in order to prevent condensation before or during measurement. Means 34 for eliminating or at least decreasing the steam content of the circulating gas flow can furthermore be placed on this line 30.

Figure 2A:
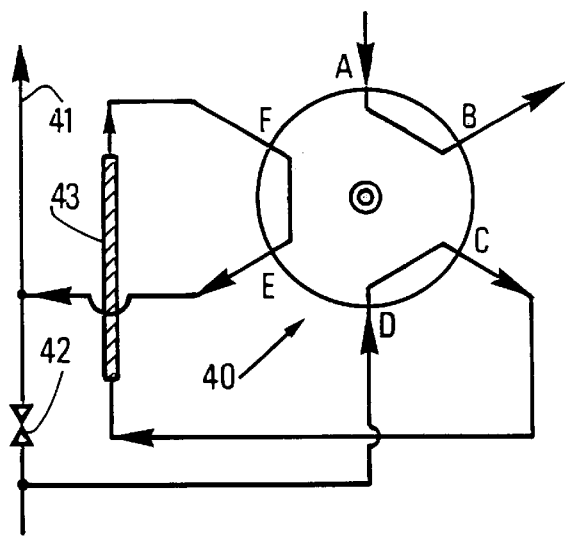
FIGS. 2a and 2b show the sampling device according to the prior art intended for analysis and measurement of the constituents in a chromatograph.
Figure 2B:
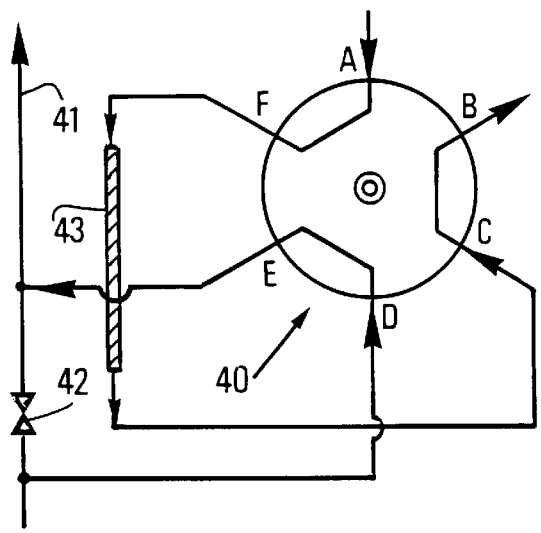

FIGS. 2a and 2b describe a conventional sampling valve 40 according to the prior art, which allows to better appreciate the considerable improvements provided by the present invention. In FIG. 2a, line 41 communicates with an atmospheric degasser (not shown), the gases taken from the fluid being displaced in line 41 by means of an air circulation. Valve 42, once closed or partially closed, diverts the effluent so that it flows through valve 40 through channels D and C, then into sampling loop 43 prior to flowing back through the valve through channels F and E and to rejoining main line 41. Channel A is connected to a carrier gas (air, helium, hydrogen or nitrogen) supply. Channel B is connected to the chromatographic analyzer. FIG. 2b shows the circuit in analysis position. The position of the ball of valve 40 has been changed so that the carrier gas in A communicates with channel F to displace the effluent trapped in loop 43 towards the analyzer at B by passing through channel C. A bypass line of line 41 passes through channels D and E. The volume of gas sent into the analyzer is about some ten microlitres ($10^{-6}$ l) at a pressure very close to the atmospheric pressure.

Figure 3A:
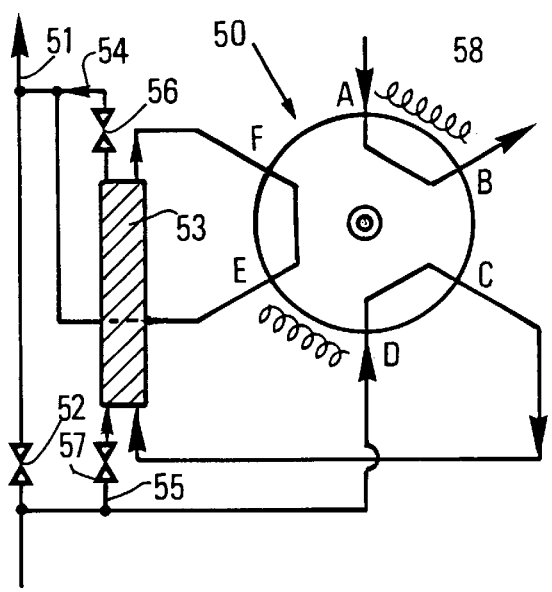
FIGS. 3a and 3b show the sampling device according to the invention intended for analysis and measurement of the constituents in a chromatograph under the present conditions.
Figure 3B:
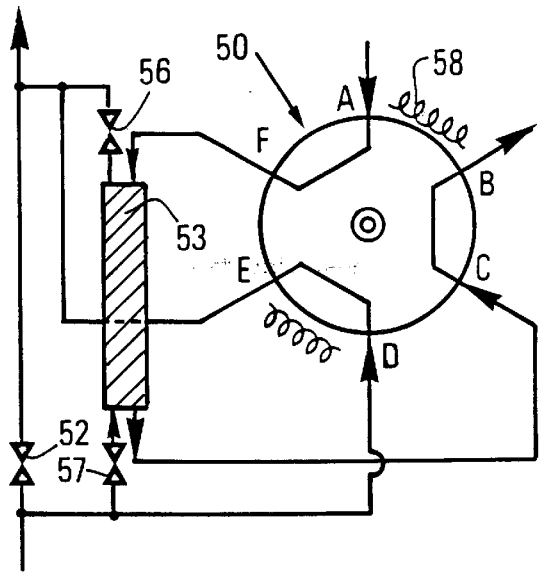

FIG. 3a shows a sampling valve 50 that can be similar to valve 40 of the prior art. Line 51 is placed under underpressure since it is connected to a vacuum pump. A sampling loop 53 can be connected to the line and to valve 50 as in the prior art, but lines 55 and 54 furthermore communicate directly with partial vacuum line 51. Controlled valves 56 and 57 open or close these communications. The volume of sampling loop 53 is much greater than that of the prior art since the volume of the effluent is low at absolute pressure. In the embodiment described here, the volume of loop 53 is about 1000 $\mu$l. In FIG. 3a, valve 50 is in sampling position, the effluent sucked by the vacuum pump flows through loop 53 by means of direct bypass lines 55 and 54, valves 56 and 57 being open. Valve 52 can be more or less closed, according to the pressure drop required. If need be, the bypass line passing through C, D, F and E is always in operation. Thus, by selecting a sufficient inside diameter for lines 55 and 54, the high pressure drops in the valve, due to the partial vacuum required for the present invention, are minimized. FIG. 3b shows the circuits in analysis position. Valves 56 and 57 are closed, the sampling valve delivers the carrier gas from channel A to channel F so as to push the effluent contained in loop 53 towards the chromatographic analyzer at B. Preferably, valve 52 is sufficiently open so that the underpressure is not limited by the pressure drops in circuits D and E. The effluent contained in the loop is partly compressed by the carrier gas, which imposes control of the temperature in all these circuits, loops and valves, so as to prevent condensation of the constituents in the effluent. A heating system 58 maintains a sufficient temperature of about 200° C. for example.

In order to test the system according to the invention, the following measurements were performed on a model comprising a 100-m or 200-m line having an inside diameter of 10 mm. A valve intended for control of the incoming air flow is mounted on a first end of this line. Pressure Pe is measured at this end Pressure Ps is measured at the other end that is extended by a 5.7-m tube with an inside diameter of 6 mm, connected to a vacuum pump where pressure Pppe is also measured.

According to the air flow rate (measured at atmospheric pressure and at ambient temperature), the absolute pressure values are given in the table hereafter:

| Flow rate (ml/min) | Pppe (mb) | Ps (mb) | Pe − (L = 100 m) (mb) | Pe − (L = 200 m) (mb) |
|---|---|---|---|---|
| 200 | 3 | 19 | 29 | 38 |
| 400 | 4 | 26 | 42 | 53 |
| 600 | 5 | 34 | 53 | 65 |
| 800 | 6 | 40 | 62 | 76 |

It is clear that the system according to the invention allows to apply an absolute pressure of some ten millibars in the extraction means, which is generally sufficient for <<heavy>> C5–C8 hydrocarbons. It can be reminded here that the sampling loop of the present invention is designed and arranged on the transport line so as not to provide a noticeable pressure drop on the line.

The time of transit of the constituents should not exceed about 120 seconds for the system to be operational. In order to assess the transit time, a determined gaseous mixture is injected at one end of the line and the appearance of this mixture is detected with a mass spectrograph connected to the other end. The following values were obtained with a 100-m long and 10-mm diameter transport line:

| Flow rate (atm.) (ml/min) | Pe (mb) | Pppe (mb) | Transit time (s) |
|---|---|---|---|
| 282 | 36 | 3.6 | 56 |
| 197 | 29 | 3 | 72 |
| 140 | 25 | 2.5 | 85 |
| 86 | 21 | 1.9 | 109 |
| 60 | 17 | 1.6 | 142 |

These measurements allow to validate an operation optimization model that takes into account the volume of gas extracted, including the steam, according to the P and T conditions previling in the extraction means. If the volume of gas sucked is not sufficient to obtain an acceptable transit time, it is possible to either heat the fluid with electrode 8 (FIG. 1) in order to obtain more steam or to allow an additional gas by controlling the opening of valve 25 and the incoming flow. A quantification representative of the content of the constituents carried along by the drilling fluid is preferably obtained without any external gas supply through line 24 (FIG. 1). It is however possible to work with an external gas, air or nitrogen, supply insofar as calibration of the measuring system is possible.

The cnditions of extraction, transport and analysis of the C1–C8 constituents are variable and depend on the nature of the drilling fluid, on the nature of the formations crossed by borehole, on the rate of circulation of the drilling fluid, on the tamperature of the fluid and of the ambient air. The system according to the invention therefore affords the advantage of allowing a high adjustment flexibility, whether for the P and T conditions during extraction, the flow rate and pressure conditions for the transit time or the injection of a sample into the chromatographic analyzer.

In order to complete the tests carried out with the model described above, pressure and transit time measurements were performed with incorporation of the sampling loop as described above. The pressure drop dp is furthermore measured at the ends of valve 52 (FIG. 3a, or 3b), i.e. at the ends of sampling loop 53 under the most unfavourable conditions, i.e. valves 56 and 57 closed.

| Flow rate (Nml/min) | Pe (mb) | Ps (mb) | Dp (mb) | Pppe (mb) | Transit time (s) |
|---|---|---|---|---|---|
| 140 | — | — | 0 | — | 85* |
| 140 | 27 | 18 | 8* | 1.9 | 108 |
| 140 | 34 | 28 | 16 | 1.9 | 134 |
| 140 | 42 | 37 | 26 | 1.8 | 160 |
| 140 | 51 | 47 | 36 | 1.8 | 197 |
| 140 | 68 | 65 | >50 | 1.8 | 257 |

*measurements on the line without sampling loop, by way of comparison.

These measurements show the adjustments of the pressure drop created by valve 52 so that the sampling loop receives a flow diverted from the main line, without the flow rate/pressure equilibrium being disturbed upon each sampling. It has been checked that the samples taken are really representative of the effluent transported by the main line. It is clear that valve 52 can be pilot-controlled if need be.

What is claimed is:

1. An extraction, analysis and measuring system intended for constituents carried along by a well fluid during drilling operations, characterized in that it comprises in combination:

draw-off means (4) for taking a determined volume of said fluid, extraction means (3) for extracting in vapour form said constituents contained in said volume of fluid, comprising a space placed under underpressure, a vapour transport line (14) whose first end communicates with said space, the second end being connected to a vacuum pump (21), sampling means (27) placed in the vicinity of the second end, comprising a sampling loop (53) allowing to sample a determined amount of the vapours circulating in said line, distribution means (50) for injecting said amount into analysis and measuring means (31), and control means (33) for controlling the temperature of said sampling means so as to prevent condensation of said amount of vapours.

2. A system as claimed in claim 1, wherein said space that contains the drilling fluid drawn off is sealed against the outside.

3. A system as claimed in claim 1, wherein said space comprises an inlet port (24) for an auxiliary gas, air or nitrogen for example.

4. A system as claimed in claim 1, wherein said extraction means comprise means (8) for heating said volume of fluid drawn off.

5. A system as claimed in claim 1, wherein said sampling loop (53) is mounted directly in parallel on transport line (14).

6. A system as claimed in claim 1, wherein said means for drawing off said drilling fluid comprise a suction pump (4) and/or a discharge pump (13).

7. A system as claimed in claim 1, wherein said space is at an absolute pressure ranging between 10 and 100 mb, and the suction of the vacuum pump ranges between 1 and 10 mb.

8. An extraction, analysis and measuring method intended for constituents carried along by a well fluid during drilling operations, characterized in that the following stages are carried out:

drawing off a volume of drilling fluid to place it in a space belonging to extraction means for extracting said constituents in vapour form, applying an underpressure in said space by means of a line connecting the analysis and measuring means to the extraction means, drawing off, in the vicinity of the analysis and measuring means, a determined amount of the vapours circulating in said line, injecting said amount of vapours into the analysis and measuring means, deducing the nature and/or the amount of the constituents vaporized in said extraction means.

9. A method as claimed in claim 8, wherein the underpressure and/or temperature conditions are adjusted for extraction in vapour form as a function of the drilling parameters, for example nature of the fluid, flow rate, ambient temperature, time of transit in the line.

10. A method as claimed in claim 9, wherein a feed flow rate of an auxiliary gas fed into said space is adjusted.

11. A method as claimed in claim 8, wherein an underpressure ranging between 10 and 100 mb in absolute pressure is applied in said extraction space.

* * * * *

UNITED STATES PATENT AND TRADEMARK OFFICE
CERTIFICATE OF CORRECTION

PATENT NO. : 6,443,001 B1
DATED : September 3, 2002
INVENTOR(S) : Gilbert Duriez et al.

It is certified that error appears in the above-identified patent and that said Letters Patent is hereby corrected as shown below:

<u>Title page,</u>
Item [73], Assignee, replace "Institut Francais du Petrole, Rueil-Malmaison Cedex FR" with -- Institut Francais du Petrole, Rueil-Mailmaison Cedex FR and Geoservices, LeBlanc Mesnil Cedex, France --.

Signed and Sealed this

Twenty-fifth Day of March, 2003

JAMES E. ROGAN
*Director of the United States Patent and Trademark Office*